(12) United States Patent
Kuhn et al.

(10) Patent No.: US 7,736,146 B2
(45) Date of Patent: Jun. 15, 2010

(54) MEDICAL HANDPIECE HAVING AN ANGLED SHAFT

(75) Inventors: Bernhard Kuhn, Biberach (DE); Thomas Classen, Herbertingen (DE)

(73) Assignee: Kaltenbach & Voigt GmbH, Biberach (DE)

( * ) Notice: Subject to any disclaimer, the term of this patent is extended or adjusted under 35 U.S.C. 154(b) by 264 days.

(21) Appl. No.: 11/399,094

(22) Filed: Apr. 5, 2006

(65) Prior Publication Data
US 2007/0264610 A1 Nov. 15, 2007

(30) Foreign Application Priority Data
Apr. 7, 2005 (DE) .................. 10 2005 016 049

(51) Int. Cl.
*A61C 1/08* (2006.01)
*A61C 1/12* (2006.01)

(52) U.S. Cl. ...................... 433/126; 433/133
(58) Field of Classification Search .................. 433/80, 433/105, 114, 133, 126
See application file for complete search history.

(56) References Cited

U.S. PATENT DOCUMENTS

| | | | |
|---|---|---|---|
| 2,010,421 A * | 8/1935 | Walter | 433/133 |
| 4,212,641 A * | 7/1980 | Eibofner et al. | 433/133 |
| 4,325,696 A * | 4/1982 | Rosenstatter et al. | 433/133 |
| 4,354,839 A * | 10/1982 | Schuss | 433/82 |
| 4,493,646 A | 1/1985 | Lacour et al. | 433/133 |
| 4,643,675 A * | 2/1987 | Kuhn | 433/126 |
| 4,661,060 A * | 4/1987 | Strohmaier | 433/131 |
| 5,674,068 A | 10/1997 | Eibofner | 433/114 |
| 6,030,216 A * | 2/2000 | Rosenstatter | 433/120 |
| 6,053,732 A * | 4/2000 | Sale | 433/125 |
| 6,106,287 A * | 8/2000 | Yates | 433/82 |
| 2003/0190583 A1 | 10/2003 | Kuhn | 433/131 |
| 2004/0166473 A1 | 8/2004 | Cohen | 433/105 |

FOREIGN PATENT DOCUMENTS

| | | |
|---|---|---|
| DE | 32 27 417 A1 | 2/1983 |
| DE | 44 17 810 C2 | 11/1995 |
| DE | 102 08 692 A1 | 3/2003 |

\* cited by examiner

*Primary Examiner*—Cris L Rodriguez
*Assistant Examiner*—Heidi M Eide
(74) *Attorney, Agent, or Firm*—Marshall, Gerstein & Borun LLP

(57) ABSTRACT

A medical, in particular dental-medical, handpiece, having a shaft, having a forward shaft section and a rearward shaft section, which defines an obtuse angle with regard to each other, having a working head at a forward end of the forward shaft section, which is tapered towards the working head, and having a drive shaft in the shaft, which drive shaft has a forward drive shaft section and a rearward drive shaft section, which stand in drive connection with one another, the forward end of the forward drive shaft section standing in drive connection with a tool holder moveably mounted in the working head, and the forward drive shaft section being mounted in a receiving sleeve. The receiving sleeve can be screwed in, from the rear, into the forward shaft section.

21 Claims, 2 Drawing Sheets

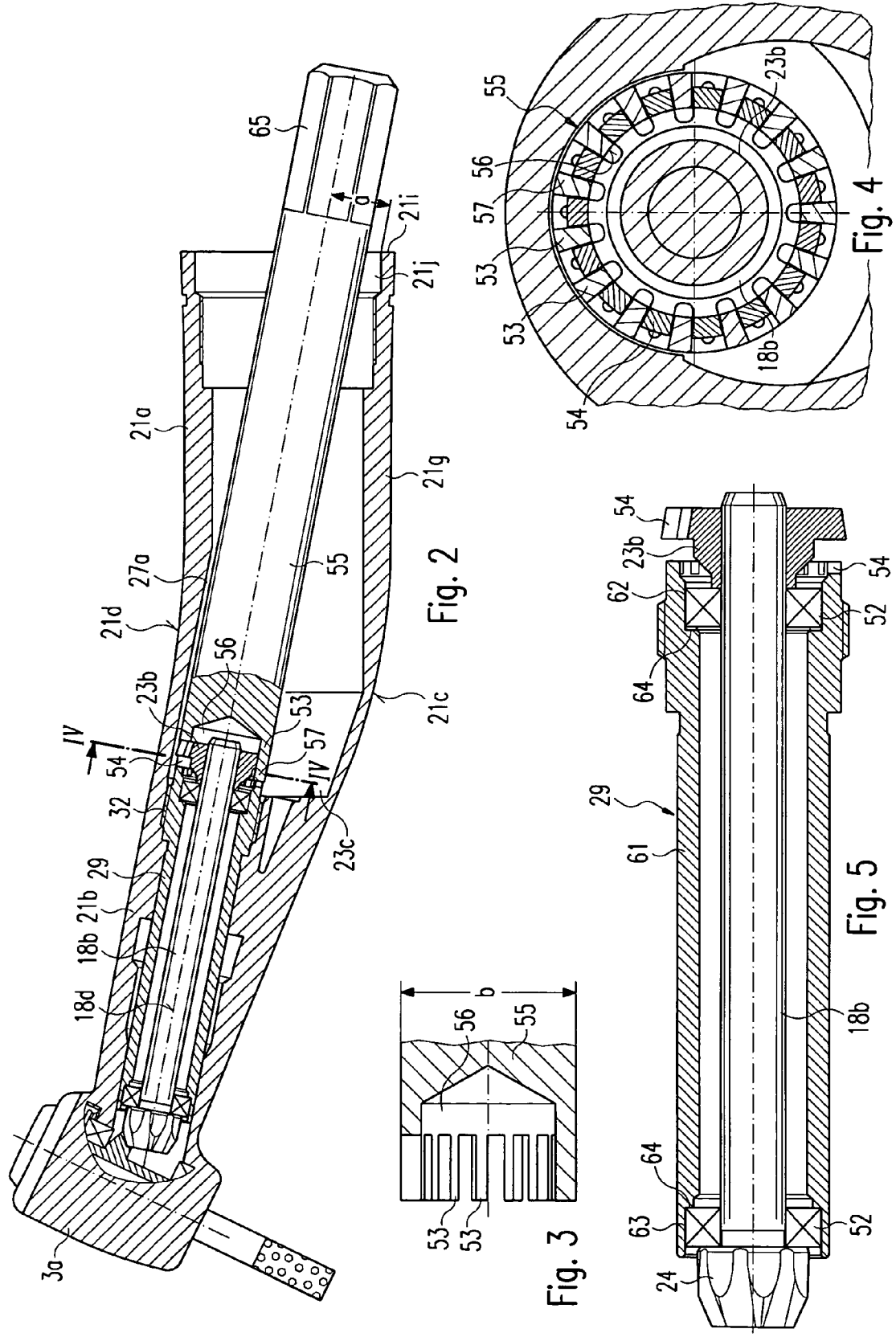

MEDICAL HANDPIECE HAVING AN ANGLED SHAFT

BACKGROUND OF THE INVENTION

1. Field of the Invention

The invention relates generally to a medical handpiece and, more specifically, to an angled dental-medical handpiece.

2. Description of Related Technology

In the case of a so-called angled handpiece concerned here, it is known, for simplification of the drive shaft, in particular of the forward drive shaft section, to transversely divide the shaft of the handpiece and connect the divided sections with one another. DE 32 27 417 A1 shows a dental-medical angled handpiece having a shaft which is transversely divided in the region of the shaft angling. In contrast, DE 44 17 810 C2 shows an angled handpiece, the shaft of which is transversely divided behind the working head, whereby the shaft in the region of the angling is formed in one piece. These divisions make possible accessibility, in particular to the forward shaft section, from the fore (DE 44 17 810 C2) or from the rear (DE 32 27 417 A1) in relation to both production measures and also installation measures. In the case of the handpiece of DE 44 17 810 C2 there further extends, in the rearward end region of the handpiece, a delivery line for a medium, passing to the outside through the peripheral wall of the handpiece, outwardly to a hose connection.

In handpieces of this type it must be taken into account that there is needed not only the ability to insert handpiece parts to be installed, in particular the forward drive shaft section, but also the need for axial fixing, in order to attain good mounting and long working life.

The above-mentioned problem does not present itself in the case of so-called turbine handpieces, having a turbine drive in the region of the working head, because in the case of a turbine handpiece the production and installation of a construction for drive shaft mounting is not needed and there is only the need to provide longitudinally running channels for the delivery and discharge of compressed air to the turbine. Thus, in the case of a turbine handpiece, a one-piece configuration of the shaft in the region of the angling or in the region between the forward shaft section and the working head is not problematic.

DE 102 08 692 A1 shows a medical handpiece whose shaft and working head are illustrated in one piece, but here there is involved a simplified illustration without indication of the necessary construction elements for the bearing and mounting of the drive shaft, in particular of the forward shaft section. In reality, there is needed also with this angled handpiece at least one transverse division, in order to allow production and assembly.

GENERAL DESCRIPTION OF THE INVENTION

The invention is provides, in the case of a handpiece of the kind described above, improved ease of assembly in a simple, economical, and compact construction. Further, the invention provides an improved solution relating to the arrangement of the media line extending on the outside of the handpiece sleeve.

The configurations in accordance with the invention are based on the insight that an installation of the receiving sleeve from the fear, into a forward shaft section, is favorable and that thereby also an axial fixing of the receiving sleeve allows itself to be achieved.

With the handpiece in accordance with one embodiment of the invention, the receiving sleeve can be screwed in from the rear, into the forward shaft section. Through this there is possible not only a simple assembly from the rear, but also a reliable axial positioning of the receiving sleeve, because through the screwing in not only is the axial positioning of the receiving sleeve ensured, but also its bringing into its axial end position, into which it reaches self-actingly upon screwing in.

In the case of another embodiment of the handpiece in accordance with the invention, the forward drive shaft section is so arranged in the shaft that its rearward end lies closer to the concave rear side of the shaft, formed through the angling of the two shaft sections, than to the convex bulge section of the same. Through this there is provided a position of the forward drive shaft section in the forward shift section which with regard to the longitudinal middle axis of the forward shaft section is offset angled towards the concave rear side of the shaft and therefore provides for the forward drive shaft section a favorable installation position with regard to the rearward shaft section likewise angled towards the concave rear side. The structural space available in the forward shaft section can thus be better-exploited with regard to a favorable position for the installation of the forward drive shaft section.

In the case of another embodiment of the handpiece of the invention, the relevant structural parameters of the handpiece are so selected that the receiving sleeve can be inserted by a linear movement through the opening at the end of the rearward shaft section, into the forward shaft section, and can there be anchored. Also with this configuration in accordance with the invention, the receiving sleeve can be mounted and dismounted from the rear, and this by a linear insertion or withdrawal movement. Thereby, the hole edge of the opening at the rearward shaft section at the convex bulge side of the shaft, is located in a position in which it has a radial spacing from the longitudinal middle axis of the receiving hole in the forward shaft section and this radial spacing corresponds at least to the greatest radial dimension of the receiving sleeve, so that this sleeve, in its linear movement, can be moved past the opening edge.

Finally, it is provided in the case of yet another the handpiece in accordance with the invention, for improved arrangement of a media line, that on the rearward end region of the peripheral wall of the handpiece there is arranged a shaft sleeve section, in that on a part of the length of the shaft sleeve section there is arranged an annular free space between it and the peripheral wall, that a delivery line for a medium passes through as a channel, and that the hose connection is arranged on the shaft sleeve section.

BRIEF DESCRIPTION OF DRAWINGS

Below, advantageous configurations of the invention will be explained in more detail with reference to preferred exemplary embodiments and drawings. There is shown:

FIG. 2 shows the handpiece in accordance with FIG. 1 in a different assembly condition;

FIG. 3 shows the forward end section of an assembly tool, in axial section;

FIG. 4 shows the part section IV-IV in FIG. 2;

FIG. 5 shows a forward receiving Sleeve, with a forward drive shaft section rotatably mounted therein, as a structural unit, in axial section.

DETAILED DESCRIPTION

Figure 1:
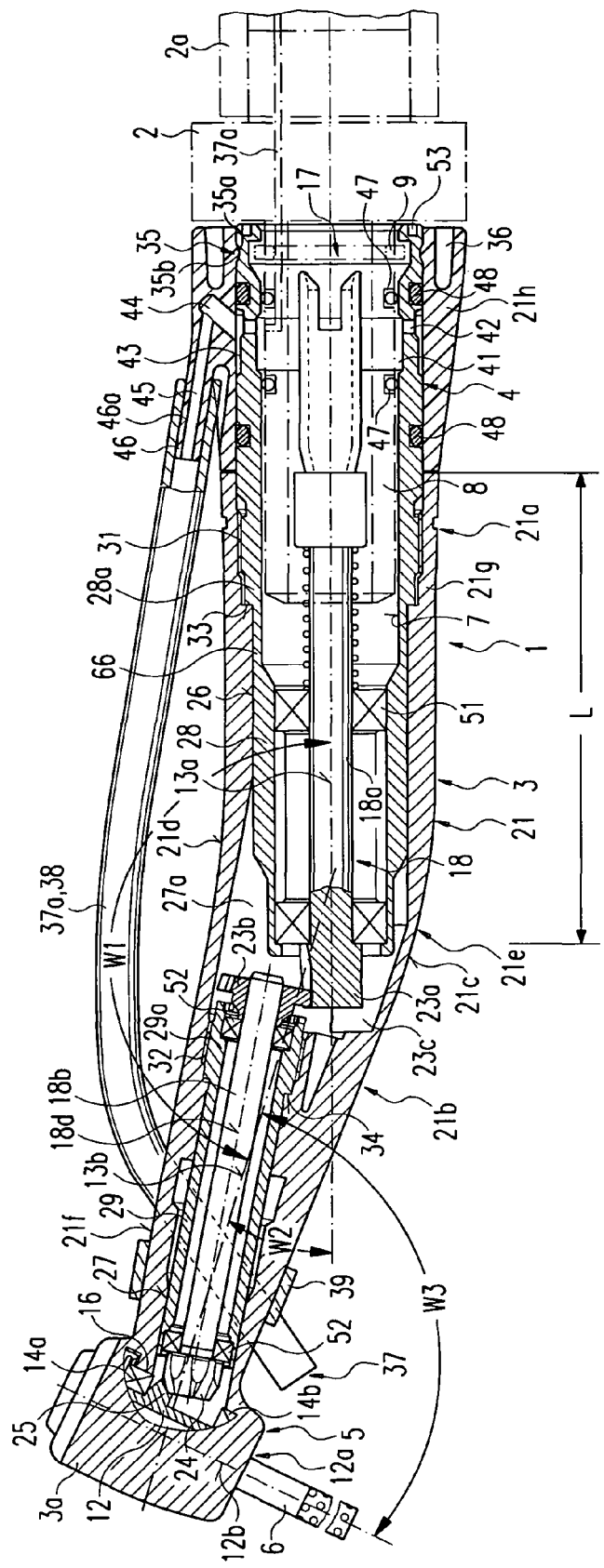
FIG. 1 shows a medical, in particular dental-medical, handpiece in accordance with the invention, in vertical longitudinal section.

The treatment instrument, generally designated in FIG. 1, includes a rearward instrument part, namely a so-called connection part 2, and a forward instrument part, namely a so-called handpiece 3, which are releasably connected with one another by a plug-in coupling 4, in particular a plug-in/turn coupling. In the forward end region of the handpiece 3 there is arranged a preferably releasable holder device 5 for a tool 6, which holds the tool 6 in a laterally projecting position. The holder device 5 forms a tool holder.

The plug-in/turn coupling is formed by a coupling recess 7, round in cross-section, and a coupling pin 8 which can be inserted therein with slight play for movement. In the case of the present exemplary embodiment, the coupling recess 7 is arranged on the rearward end of the handpiece 3, and the substantially cylindrical or stepped cylindrical pin 8 extends forwardly from the connection part 2. In the coupled condition, the coupling recess 7 and the coupling pin 8 are releasably latched with one another by a latch device having a schematically illustrated latch element 9, which is radially moveably mounted in the one coupling part and biassed by spring force into a latching position penetrating the dividing joint between the coupling parts, in which latching position the latch element 9 engages into a ring groove in the other coupling part. Such a known latch device can be overcome by manual exercise of a pulling force for the separation of the coupling parts, whereby the latch element 9 is self-actingly urged into its release position. The latch element 9 is e.g. a radially elastically compressible spring ring, which sits in an outer ring groove in the coupling pin and projects into an inner ring groove in the coupling recess.

The connection part 2 is connectable or connected, in a non-illustrated manner, with a flexible supply line 2a, which is connected with a control apparatus. The handpiece 3 is, with the plug-in/turn coupling present, mounted freely, rotatably, around 360°, on the connection part 2, through which the handling of the handpiece is improved.

The holder device 5 has a receiving sleeve 12 for receiving the tool 6, which receiving sleeve has at the end towards the tool an insertion opening 12a for the tool 6, or for its holder element, accessible from the tool side. The receiving sleeve 12 is moveably mounted, e.g. rotatably mounted, in a disposition extending transversely, e.g. at a right angle or an obtuse angle to the longitudinal middle axis 13a, 13b of the handpiece 3, in an appropriate mounting arrangement in the forward end-region of the handpiece 3. For the mounting two rotary bearings 14a, 14b, e.g. roller bearings, are arranged between mounting pins at the end side of the receiving sleeve 12 and the inner, peripheral wall of a mounting bore 16.

The receiving sleeve 12 or the holder device 5 can be moved by a drive 17 having a non-illustrated drive motor, which may be arranged within or outside the handpiece 3, e.g. in connection part 2. In the case of the exemplary embodiment there extends longitudinally through the handpiece 3 or instrument 1 a driveshaft 18, which stands in drive connection with the receiving sleeve 12 or the holder device 5.

The handpiece 3 has an elongate shaft 21, at the forward end of which a handpiece head 22 is arranged, in which the receiving sleeve 12 is rotatably mounted. The shaft 21 is of a rearward shaft section 21a and a forward shaft section 21b, which include with one another an obtuse angle W1, which is about 150 to 170°, preferably about 160 to 165°. The forward shaft section 21b is thus, with reference to the longitudinal axis 13a of the rearward shaft section 21a, angularly offset by an acute angle W2 of about 10 to 30°, in particular about 15 to 20°, to the side away from the insertion opening 12a. Through this the shaft 21 is provided with, at the side at which the insertion opening 12a is located, a convex bulge side 21c and opposite thereto a concave rear side 21d. The angling or curvature apex is designated by 21e. The forward shaft section 21b extends forwardly, convergently to a thickened working head 3a of the handpiece 3.

The longitudinal axis 12b, or the axis of rotation of the receiving 12, includes with the longitudinal middle axis 13b of the forward shaft section 12a an angle W3, which may be 90°, e.g. is greater than 90°, preferably about 95 to 115°, in particular about 105° or about 90 to 105°. These sizes of angle provide, while ensuring an advantageous grip position for the operating hand rasping the handpiece 3, a favorable form with regard to the treatment site, in particular in the mouth of a patient.

The drive shaft 18 is of a rearward drive shaft section 18a, in the rearward shaft section 21a and rotatably mounted therein, and a forward drive shaft section 18b, extending in the forward shaft section 21b and rotatably mounted therein, which in the region of the apex 21e stand in rotary connection with one another. In the case of the exemplary embodiment there serves for this purpose a gear transmission having a bevel gear 23a arranged on the forward end of the rearward drive shaft section 18a and a bevel gear 23b arranged on the rearward end of the forward drive shaft section 18b. Thereby, the forward drive shaft section 18b is, with reference to the longitudinal middle axis 13b of the forward shaft section 21b and also with reference to the forward end of the rearward drive shaft section 18a, offset towards the concave rear side 21d, so that also the bevel gear 23b at the rearward end of the forward drive shaft section 18b, with regard to the bevel gear 23b at the forward end of the rearward drive shaft section 18a, is offset towards the concave rear side 21d. Preferably, the axis of rotation 18d of the forward drive shaft section 18a is, with reference to the longitudinal middle axis 13b of the forward shaft section 21b, so far angularly offset to the concave rear side 21d, that the axis of rotation 18d extends parallel to the longitudinal envelope line 21f of the forward shaft section 21b at the concave rear side 21d.

At the forward end of the forward drive shaft section 18b there is arranged a bevel gear 24, which engages with a bevel gear 25 arranged on the receiving sleeve 12 and preferably formed thereon in one piece, which bevel gear 25 preferably engages with the bevel gear 24 at the side thereof away from the insertion opening 12a, on which side, due to the angle W3, a spatially favorable gear transmission allows itself to be realized.

For receiving and mounting the drive shaft sections 18a, 18b in the rearward and forward shaft sections 21a, 21b there serve receiving holes 26, 27 arranged therein, in which the drive shaft sections 18a, 18b are rotatably mounted, preferably by receiving sleeves 28, 29, which in each case are inserted from the rear into the associated receiving hole 26, 27 and axially fixed. The latter is in each case preferably a screw connection 31, 32, of which that of the rearward receiving sleeve 28 is located in its middle region and that of the forward receiving sleeve 29 is located in its rearward end region. The two screw connections 31, 32 in each case have an external threading on the associated sleeve and internal threading in the associated shaft section. Preferably, there are arranged screw connections 31, 32 in each case in the region of a thickening 28a, 29a of the associated sleeve and in a cross-sectional widening in the associated shaft section.

Through this there is provided for each screw connection 31, 32, at a spacing forwardly directed therefrom, a shoulder surface stop 33, 34 for the associated receiving sleeve 28, 29, through which this, in the screwed-fast condition, is axially exactly positioned and also fixed against a release. The rearward shaft section 21a is of two longitudinal sections, namely a shaft sleeve section 21g extending from the apex 21e rearwardly only over a part of the rearward receiving sleeve 28, and a shaft sleeve section 21h arranged therebehind, which extends up to the rearward end of the shaft 21 and to the rearends flush with the receiving sleeve 28 likewise extending up to the rearward end. The forward receiving sleeve section 21g is thus shorter than the rearward shaft section 21a. The rearward shaft sleeve section 21h thus sits on the rearward end region of the receiving sleeve 28, and can be pushed thereon from the rear and fixed by a fixing device against a return movement.

In the case of the exemplary embodiment, the associated fixing device is formed by a latch device 35 having a latch recess on the one component part and a latch projection, which can latch therein, on the other component part. The latch recess may be formed by a ring groove 35a in the envelope surface of the receiving sleeve 28, and the latch projection formed by a ring beading 35b on the inner envelope surface of the rearward shaft sleeve section 21h. The latch device 35 can be overcome by the action of an axial force upon pushing on or pushing off of the rearward shaft sleeve section 21h, i.e. upon axial movement the latch projection provides a certain resistance, which however is overcome by the action of axial force, and this both in the case of latching-in into the latch recess 35a and also upon latching-out. The latch recess 35 is preferably arranged at a short spacing from the rearward end of the shaft sleeve section 21h and the receiving sleeve 28. In the shaft sleeve section 21h there is arranged a ring groove 36 surrounding the latch device 35, which groove opens outwardly and can improve the flexibility of the latch device 35.

The rearward shaft sleeve section 21h is preferably of plastic, through which the flexibility is improved and also benefits the latch device 35. The shaft sleeve section 21h is at least at its rearward end region thicker than the rearward shift section 21a and it tapers forwardly to a sleeve thickness which corresponds to that of the forward sleeve section 21d, so that these two parts transition into one another with their outer envelope surfaces at the dividing joint.

With the handpiece there is associated a delivery device, designated in its entirety by 37, for a gaseous or liquid medium, such as e.g. air, water or an air-water mixture, having a delivery line 37a which extends longitudinally through the supply line 2a, the connection part 2 and through the coupling 4 up into the forward end region of the handpiece 3, and is directed onto the treatment site. In the case of the exemplary embodiment, the delivery line 37a runs, with the exception of the rearward handpiece region, outside the handpiece 3, and it is formed in this external region by a hose 38, which extends from a hose connection 46 in the rearward end region of the handpiece 3 into the forward end region, and in the forward end region is connected with a C-shaped clip 39, which is transversely clipped onto the forward shaft section. 21b.

To this hose connection 46, the delivery line 37a extends initially axially in the connection part 2 and in the coupling pin 8, in the region of which it radially opens out, and this into a ring groove 41 arranged between the coupling pin 8 and the receiving sleeve 28, which ring groove is preferably arranged in the inner envelope surface of the receiving sleeve 28. From the ring groove 41, the delivery line 37a extends in the form of one or more holes 42, arranged distributed on the periphery, into a ring groove 43 between the receiving sleeve 28 and the rearward shaft sleeve section 21h, whereby the ring groove 43 is preferably arranged in the envelope surface of the receiving sleeve 28. From the ring groove 43 there extends a hole 44, in the rearward shaft sleeve section 21h, outwardly, from which a channel 45 extends towards the hose connection 46, which in the case of the exemplary embodiment is formed by a hose nozzle, preferably formed on in one piece on the shaft sleeve section 21h and extending e.g. axially or obliquely forwardly, onto which hose nozzle the hose 38 is inserted and thus connected. The channel 44 thus extends preferably so obliquely that it can be bored in from the forward end of the shaft sleeve section 21h (illustrated) or from the rearward end (not illustrated).

For sealing the ring grooves 41, 43 there are arranged ring seals between the coupling pin 8 and the receiving sleeve 28 and also between this and the shaft sleeve section 21h. These ring seals may be formed by O-rings 47, 48 arranged in ring grooves. In the case of the ring grooves these may be inner ring grooves in the shaft sleeve section 21h or in the receiving sleeve 28 (not illustrated), or outer ring grooves in the receiving sleeve 28 and in the coupling pin 8, as is illustrated.

The receiving sleeves 28, 29 form, in each case with the drive shaft sections rotatably mounted therein and in each case two roller bearings arranged at an axial spacing from one another, and the associated gears, a prefabricatable sleeve structural unit which in the case of initial installation or also in the case of an exchange can be simply and rapidly installed or exchanged. For screwing in or screwing out there are arranged on the two receiving sleeves 28, 29, in each case at the rearward end and accessible from the rear, rotary engagement elements 53, 54, with which in each case a rotary tool 55 can be connected in a form-fitting manner. FIG. 2 shows a pin-like rotary tool 55, which at its forward end is formed sleeve-like with a hollow space 56 arranged in the sleeve shape. With this sleeve shape, the rotary tool 55 is suitable for engaging over the bevel gear 23b and to engage on the rearward rotary-engagement elements 54 at the receiving sleeve 29. The rotary engagement elements 54 are preferably formed by teeth and tooth spaces arranged therebetween, which are arranged distributed over the entire periphery of the receiving sleeve 29 and are accessible axially from the rear.

When the bevel gear 23b is so large that it obscures the accessibility of the rotary engagement elements 54 from the rear, it is to be formed with teeth and tooth spacings in the same number as the teeth and spacings of the bevel gear 23b. With such a configuration, the teeth 57 of the rotary tool 55 can be placed through the tooth spacings of the bevel gear 23b into the tooth spacings of the rotary engagement elements 54 and thus connected with these in a form fitting manner. This configuration makes it possible, with the restricted spatial conditions of a dental-medical handpiece 3, despite a relatively large configuration of the bevel gear 23b, to ensure accessability to the rotary engagement elements 54 of the receiving sleeve 29.

The forward receiving sleeve 29, prefabricated as a self-contained structural unit, is of a sleeve body 61, the drive shaft section 18b with the bevel gears 24, 54 arranged thereon at the end, and two rotary bearings 52, in particular roller bearings, which sit on the drive shaft section 18b in the two end regions thereof, and are put in place in bearing bores 62, 63, towards the ends, in each case from the associated sleeve body end, and thereby bear with their outer rings inwardly on a shoulder surface 64 of the bearing bores 62, 63, whereby the bevel gears 24, 54 bear on the outer side of the inner rings of the rotary bearing 52. By means of this configuration, the above-described parts of the receiving sleeve 29 are axially and radially determined, taking into account a necessary play for movement. The receiving sleeve 29 thus forms a pre-installed structural unit, which selectively is insertable and screwable into the forward shaft section 21b from the rear and can be axially fixed against the shoulder surface stop 34. The screwing in prom the rear is possible because in the rearward shaft section 21a so much free space is present that the receiving sleeve is installable as described above.

In the case of the present exemplary embodiment, the rearward edge 21i of the opening 21g of the receiving sleeve section 21g has a spacing a from the imaginary extension of the rotary and longitudinal middle axis 18d of the forward drive shaft section 18b, which is so large that the receiving sleeve 29 can be introduced and screwed in, and again removed, with a coaxial movement from the rear. In the stop position, the bevel gears 24, 25 stand in engagement between the forward driveshaft section 18b and the receiving sleeve 12.

For screwing fast and screwing apart the receiving sleeve 29, there serve the rotary engagement elements 54 at the rearward end of the sleeve body 61, which are accessable from the rear with a rod-shaped rotary tool 55, which at its rearward end likewise has a rotary engagement device 65, e.g. a hexagonal tool, and is so long that it is accessable from the rear. In the case of the exemplary embodiment, the rotary tool 55 projects beyond the rearward edge 21i with the rotary engagement device 65. The rotary tool 55 has approximately the same cross-sectional size as the receiving sleeve 29, in particular in the region of its thickening 29a. Thus, the rotary tool 55 can also be moved into working position with a coaxial arrangement, with regard to the axis of rotation 18d, and linear delivery movement to the rotary engagement element 54, and functionally appropriately rotated.

The cross-sectional dimension b of the rotary tool 55, in its forward end region, is in the case of the present exemplary embodiment, in which the bevel gear 23b obscures the end side of the sleeve body 61 from the rear, matched to the outer diameter of the bevel gear 23b. The rotary engagement elements 53 on the rotary tool 55 are formed by teeth projecting forwardly from its end side, which are so adapted to the size of the tooth spaces of the bevel gear 23b that they can be inserted through the tooth spaces and extend up to between the rotary engagement elements 54 at the rearward end of the sleeve body 61, which are preferably formed by rearwardly projecting teeth, which are likewise so configured that the teeth of the rotary tool 55 can be inserted between the teeth of the sleeve body 61. By the insertion, the bevel gear 23b is taken up in the hollow space 56 of the rotary tool 55, through which the rotary tool 55 receives a guidance which transversely positions the rotary tool 55 and hinders a dislocation from tooth engagement.

The rearward receiving sleeve 28, illustrated only in FIG. 1, is likewise formed by a sleeve body 66, which can be inserted from the rear into the receiving hole 26 of the rearward shaft section 21a and which in two rotary bearings 51 mounts the rearward drive shaft section 18a, which rotary bearings have an axial spacing from one another and are arranged in the forward half of the sleeve body 66. The rearward drive shaft section 18b, with the bevel gear 23a mounted at its forward end, is inserted with the roller bearings 51 from the rear into the sleeve body 66 and axially fixed. In the position screwed in against the shoulder surface stop 33, and thus axially fixed position of the receiving sleeve 28, the bevel gear 23a is located with reference to the bevel gear 23b in its correct axial engagement position. For the screwing in and screwing out of the receiving sleeve 28 there are provided at its rearward end rotary shaft section 18a which, with regard to the rearward bevel gear 23b of the forward drive shaft section 18b, is offset towards the bulge side 21c. The two bevel gears 23a, 23b thus engage at the rearward side of the forward bevel gear 23a and the bulge side of the rearward bevel gear 23b of the drive shaft-sections 18a, 18b. Here also the available inner space allows itself to be exploited for the desired space utilization in that in the region of the angled apex the receiving hole 26 extends into the rearward end region of the forward shaft section 21b and in the angled region forms a free space 23c for the bevel gears 23a, 23b engaging with one another. At the rearward side, the receiving hole 27 is extended rearwardly into the transition region of the rearward shaft section 21a. Through this a free space 27a is provided, through which the rotary tool 55 can be inserted.

In the case of the present exemplary embodiment a further structural parameter is that the rearward shaft section 21a can be shortened to a length L, with which the coaxial accessability to the forward drive shaft section 18b, or to the forward receiving sleeve 29, is ensured. This shortening is effected by dismounting the drive shaft section 21h and the rearward sleeve section 28. In the case of a so shortened handpiece 3 or shaft 21 in accordance with FIG. 2 there is not only ensured the accessability to the forward drive shaft section 18b or the forward receiving sleeve 29, but also or the rotary tool 55, due to the spacing a.

The accessability allows itself thus to be improved in that the rearward drive shaft section 21b can be shortened, so that for the edge 21e at the bulge side 21c a more favorable position is provided with regard to the alignment with the forward receiving sleeve 29, in which the forward receiving sleeve 29 or the rotary tool 55 are, of the forward drive shaft section 18d or of the forward receiving sleeve 29 is more favorable with regard to the rearward edge of the receiving hole 26 in the rearward shaft section 21a.

It is thus possible to so position the rearward edge of the receiving hole 26 at the bulge side 21c, by appropriate crosssectional dimensions of the forward receiving sleeve 29, of the receiving hole 26, and of the axial spacing of the rearward edge of the receiving hole 26 at the bulge side 21c, that the hole edge has the spacing a to the extension of the longitudinal middle axis of the forward receiving sleeve 29, which is the same as or greater than half the cross-sectional dimension of the receiving sleeve 29 and/or of the rotary tool 59, so that these parts can with coaxial movement, with reference to the longitudinal middle axis of the receiving sleeve 29, be installed or removed, or with regard to the rotary tool 59 brought into working position and again removed.

The rotary axis 18d or the longitudinal middle axis of the forward drive shaft 18b or the forward receiving sleeve 29 extends preferably parallel to the outer side of the forward shaft section 21b at the concave rear side 21d. Through this, the available inner space of the shaft 21 can be particularly favorably-exploited.

In contrast, the rotary axis 13a of the rearward drive shaft section 18b or the longitudinal middle axis of the rearward receiving sleeve 29 extends coaxially in the rearward shaft section 21a, which extends at least in its forward region with the same cross-sectional size. Taking into account the angling between the shaft sections, there is thereby provided a position for the forward bevel gear 23a of the rearward drive engagement elements 53, which are accessible for a nonillustrated rotary tool and e.g. are formed by holes opening out to the rear.

The rearward shoulder surface stop 33 for the rearward receiving sleeve 28 in the rearward shaft section 21a and the forward shoulder surface stop 34 for the forward receiving sleeve 29 in the forward sleeve section 21d are located in longitudinal positions in the shaft 21 in which the pre-installed receiving sleeves 28, 29 are so arranged that the rearward bevel gear pair 23a, 23b and the forward bevel gear pair 24, 25 are located in the correct engagement positions. An axial alignment of the receiving sleeves 28, 29 is thus not necessary.

In addition to the above-described structural parameters, which ensure the introduction and screwing in or screwing out of the forward receiving sleeve 29 from the rear, the following structural parameters will be described, which further improve this accessability from the rear.

The forward drive shaft section 18b is so arranged in the forward shaft section 21b, that the rearward end of the forward drive shaft section 18b lies closer to the concave rear side 21d of the shaft 21, formed by the angling of the two shaft sections 21a, 21, than to the convex bulge side 21c. The rearward end of the forward drive shaft section 18d, or of the forward receiving sleeve 29, is thus, with regard to per se known configurations, with which the middle or rotary axis 18d of the drive shaft section 18b is arranged coaxially to the longitudinal middle axis 13b of the forward shaft section 21b, angularly offset towards the rear side 21d. By this angular offset, the accessibility from the rear is improved, because the position of the rearward end in substance by coaxial movements, installable or removable from the rear, or can be brought into functional disposition or removed from the functional disposition. After the installation of the forward receiving sleeve 20, the rearward shaft section 21b can be again extended, which in the case of the exemplary embodiment is effected by the installation of the rearward receiving sleeve 28. Already through this, the extension of the rearward shaft section 21a can be completed, whereby the rearward shaft section 21a can extend up to the rearward end of the installed rearward receiving sleeve 28.

In the case of the present exemplary embodiment there is additionally present the sleeve shaft section 21h, which can be withdrawn to provide a shortening and again pushed on to provide an extension. For axial positioning of the sleeve shaft section 21h there serves a quick-fastening connection, which in the case of the exemplary embodiment is formed by a latch connection 35 and makes possible a rapid and ready withdrawal and re-emplacement of the sleeve shaft section 21h.

The invention claimed is:

1. Medical handpiece comprising:
a one-piece shaft having a forward shaft section and a rearward shaft section defining an obtuse angle with respect to each other, the forward shaft section and the rearward shaft section each having a longitudinal middle axis,
a working head disposed at a forward end of the forward shaft section, the forward shaft section being tapered towards the working head,
a drive shaft in the shaft, the drive shaft having a forward drive shaft section and a rearward drive shaft section, the forward and rearward drive shaft sections being in drive connection with one another and angularly offset with respect to one another, and an axis of rotation of the forward drive shaft section being arranged so that the axis of rotation is angularly offset with respect to the longitudinal middle axis of the forward shaft section,
a forward end of the forward drive shaft section standing in drive connection with a tool holder movably mounted in the working head, and,
the forward drive shaft section being mounted in a receiving sleeve,
wherein the rearward shaft section defines a receiving hole for receiving the forward drive shaft section and the receiving sleeve during assembly of the handpiece or replacement of the forward drive shaft section and the receiving sleeve,
wherein the receiving sleeve can be screwed, from the rear, into the forward shaft section, and
wherein a rearward edge of the receiving hole proximate a convex bulge side of the one-piece shaft is spaced from the axis of rotation of the forward drive shaft section by a distance of at least half of a cross-sectional dimension of the receiving sleeve.

2. Handpiece according to claim 1, wherein the forward drive shaft section is disposed in the shaft such that a rearward end thereof lies closer to a concave rear side of the shaft, formed by the angle of the two shaft sections than to the convex bulge side of the shaft.

3. Handpiece according to claim 1, wherein the receiving sleeve can be inserted by a linear movement through the receiving hole at the end of the rearward shaft section into the forward shaft section.

4. Medical handpiece comprising:
a one-piece shaft having a forward shaft section and a rearward shaft section defining an obtuse angle with respect to each other, the forward shaft section and the rearward shaft section each having a longitudinal middle axis, and the rearward shaft section defining a receiving hole,
a working head disposed at a forward end of the forward shaft section, the forward shaft section being tapered towards the working head,
a drive shaft in the shaft, the drive shaft having a forward drive shaft section and a rearward drive shaft section the forward and rearward drive shaft sections being in drive connection with one another and angularly offset with respect to one another, and an axis of rotation of the forward drive shaft section being arranged so that the axis of rotation is angularly offset with respect to the longitudinal middle axis of the forward shaft section,
a forward end of the forward drive shaft section standing in drive connection with a tool holder movably mounted in the working head, and,
the forward drive shaft section being mounted in a receiving sleeve,
wherein the forward drive shaft section is disposed in the shaft such that a rearward end thereof lies closer to a concave rear side of the shaft, formed by the angle of the two shaft sections, than to a convex bulge side of the shaft,
and a rearward edge of the receiving hole proximate the convex bulge side of the shaft is spaced from the axis of rotation of the forward drive shaft section by a distance of at least half of a cross-sectional dimension of the receiving sleeve.

5. Handpiece according to claim 4, wherein the receiving sleeve can be installed from the rear of the one-piece shaft.

6. Medical handpiece comprising:
a one-piece shaft having a forward shaft section and a rearward shaft section defining an obtuse angle with respect to each other, the forward shaft section and the rearward shaft section each having a longitudinal middle axis and the rearward shaft section defining a receiving hole,
a working head disposed at a forward end of the forward shaft section, the forward shaft section being tapered towards the working head, a drive shaft in the shaft, the drive shaft having a forward drive shaft section and a rearward drive shaft section, the forward and rearward drive shaft sections being in drive connection with one another and angularly offset with respect to one another, and an axis of rotation of the forward drive shaft section being arranged so that the axis of rotation is angularly offset with respect to the longitudinal middle axis of the forward shaft section, a forward end of the forward drive shaft section standing in drive connection with a tool holder movably mounted in the working head, and, the forward drive shaft section being mounted in a receiving sleeve, wherein the receiving sleeve can be inserted by means of a linear movement through the receiving hole at the end of the rearward shaft section into the forward shaft section, and a rearward edge of the receiving hole proximate a convex bulge side of the one-piece shaft is spaced from the axis of rotation of the forward drive shaft section by a distance of at least half of a cross-sectional dimension of the receiving sleeve.

7. Handpiece according to claim 6, wherein the receiving sleeve can be screwed in from the rear into the forward shaft section.

8. Handpiece according to claim 1, comprising disposed at the rearward end of the receiving sleeve, rotary engagement elements which are accessable from the rear for a rotary tool.

9. Handpiece according to claim 1, wherein the rearward drive shaft section is mounted in a rearward receiving sleeve, which is insertable from the rear into the rearward drive shaft section and is fixable.

10. Handpiece according to claim 1, wherein the receiving sleeve bears in a forward direction on a shoulder surface stop.

11. Handpiece according to claim 4, comprising disposed at the rearward end of the receiving sleeve, rotary engagement elements which are accessable from the rear for a rotary tool.

12. Handpiece according to claim 4, wherein the rearward drive shaft section is mounted in a rearward receiving sleeve, which is insertable from the rear into the rearward drive shaft section and is fixable.

13. Handpiece according to claim 4, wherein the receiving sleeve bears in a forward direction on a shoulder surface stop.

14. Handpiece according to claim 6, comprising disposed at the rearward end of the receiving sleeve, rotary engagement elements which are accessable from the rear for a rotary tool.

15. Handpiece according to claim 6, wherein the rearward drive shaft section is mounted in a rearward receiving sleeve, which is insertable from the rear into the rearward drive shaft section and is fixable.

16. Handpiece according to claim 6, wherein the receiving sleeve bears in a forward direction on a shoulder surface stop.

17. Handpiece according to claim 1, wherein the receiving sleeve surrounds at least one bearing and a portion of the forward drive shaft section.

18. Handpiece according to claim 17, wherein the at least one bearing is seated in a bearing bore formed in an inner surface of the receiving sleeve.

19. Handpiece according to claim 1, wherein the axis of rotation of the forward drive shaft section extends substantially parallel to an outer surface of the forward shaft section along a concave side of the forward shaft section.

20. Handpiece according to claim 8, wherein the rotary engagement elements comprise a plurality teeth and tooth spaces distributed over a periphery of the receiving sleeve.

21. Handpiece according to claim 20, wherein the number of teeth and tooth spaces is equal to the number of teeth and tooth spaces of a bevel gear mounted at the rearward end of the forward drive shaft section.

* * * * *